United States Patent [19]
Harris

[11] Patent Number: 6,063,962
[45] Date of Patent: May 16, 2000

[54] PROCESS FOR THE PREPARATION OF NMDA ANTAGONISTS

[75] Inventor: Alan Richard Harris, Shepshed, United Kingdom

[73] Assignee: Astra Pharmaceuticals Limited, Herts, United Kingdom

[21] Appl. No.: 09/011,777

[22] PCT Filed: Dec. 12, 1997

[86] PCT No.: PCT/SE97/02092

§ 371 Date: Feb. 24, 1998

§ 102(e) Date: Feb. 24, 1998

[87] PCT Pub. No.: WO98/27052

PCT Pub. Date: Jun. 25, 1998

[30] Foreign Application Priority Data

Dec. 19, 1996 [GB] United Kingdom .................. 9626319

[51] Int. Cl.[7] ..................... C07C 231/14; C07C 231/02; C07C 231/12

[52] U.S. Cl. ............................. 564/195; 560/41; 560/157; 560/160; 564/196

[58] Field of Search ..................................... 564/196, 195; 560/41, 157, 160

[56] References Cited

FOREIGN PATENT DOCUMENTS 0 279 937  8/1988  European Pat. Off. .
955 508   1/1957  Switzerland .

OTHER PUBLICATIONS

Wender et al, "The Intramolecular Addition of Silylated Alkynes to Aldehydes: Methodology . . . ," Tetrahedron Letters, vol. 36, No. 2, pp. 209–212 (1995).

*Primary Examiner*—Peter O'Sullivan
*Attorney, Agent, or Firm*—Nixon & Vanderhye

[57] ABSTRACT

This invention relates to an improved process for the production of known amine compounds which are useful as medicaments.

16 Claims, No Drawings

PROCESS FOR THE PREPARATION OF NMDA ANTAGONISTS

This application is a 371 of PCT/SE97/02092 Dec. 12, 1997.

This invention relates to an improved process for the production of known amine compounds which are useful as medicaments.

European Patent EP 279937 describes a group of compounds which are indicated as anticonvulsants. The compound of Example 1, 2-amino-N-(1,2-diphenyl-1-methylethyl)acetamide hydrochloride (which has the INN Remacemide hydrochloride), is undergoing clinical trials.

Known processes for the production 2-amino-N-(1,2-diphenyl-1-methylethyl)acetamide and its analogues have the disadvantage of low yields. Example 1 of European Patent EP 279937 provides 2-amino-N-(1,2-diphenyl-1-methylethyl)acetamide hydrochloride in only 32% yield based on the 1,2-diphenyl-2-propylamine starting material. The process in question comprises coupling of Cbz-glycine with 1,2-diphenyl-2-propylamine in the presence of DCC, followed by removal of the Cbz group by hydrogenolysis.

In addition, the products of such known processes require considerable purification before they can be used in pharmaceutical formulations. It has now surprisingly been found that a different process has the advantage of greatly improved yield and, furthermore, provides the desired product with good purity.

In a first aspect the present invention therefore provides a process for the production of a compound of formula (I) or a pharmaceutically acceptable salt thereof:

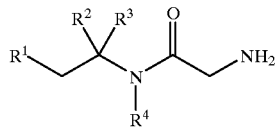
(I)

wherein:
$R^1$ and $R^2$ are independently phenyl or 4-fluorophenyl;
$R^3$ is hydrogen, alkyl $C_{1-4}$ or methoxycarbonyl;
$R^4$ is hydrogen or methyl;
which comprises reaction of a compound of formula II:

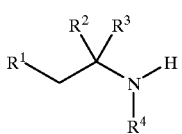
(II)

in which $R^1, R^2, R^3$ and $R^4$ are as defined in formula (I), with a compound of formula (III):

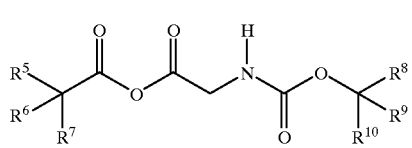
(III)

in which $R^5, R^6, R^7, R^8, R^9$ and $R^{10}$ are independently $C_{1-6}$ alkyl to give a compound of formula (IV):

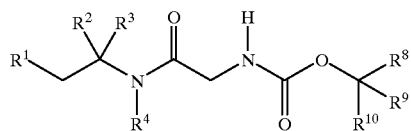
(IV)

in which $R^1, R^2, R^3, R^4, R^8, R^9$ and $R^{10}$ are as defined in formula (I), followed by deprotection and optionally thereafter forming a pharmaceutically acceptable salt.

Pharmaceutically acceptable salts of the compounds of formula I include acid addition salts, in particular hydrochloride salts. Such salts are prepared using standard procedures known in the art.

Suitably $R^1$ and $R^2$ are independently phenyl or 4-fluorophenyl, preferably $R^1$ and $R^2$ are both phenyl.

Suitably $R^3$ is hydrogen, $C_{1-4}$ alkyl or methoxycarbonyl, preferably $R^3$ is $C_{1-4}$ alkyl, in particular methyl.

Suitably $R^4$ is hydrogen or methyl, preferably $R^4$ is hydrogen.

Most preferably the above process is used to prepare the compound of formula I which is 2-amino-N-(1,2-diphenyl-1-methylethyl)acetamide, or a pharmaceutically acceptable salt thereof. Suitable salts include acid addition salts such as hydrohalide salts, preferably the hydrochloride salt.

Suitably $R^1, R^2, R^3, R^4, R^8, R^9$ and $R^{10}$ are independently $C_{1-6}$ alkyl, preferably $R^1, R^2, R^3, R^4, R^8, R^9$ and $R^{10}$ are all methyl, such that $R^8, R^9$ and $R^{10}$ forms part of a Boc protecting group.

The mixed anhydrides of formula (III) are prepared by reacting a compound of formula (V):

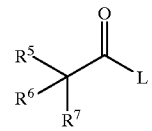
(V)

in which $R^5, R^6$ and $R^7$ are as defined in formula (III) and L is a leaving group with a compound of formula (VI):

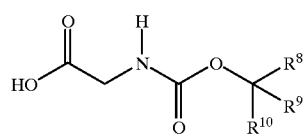
(VI)

in which $R^8, R^9$ and $R^{10}$ are as defined in formula (III). Suitably L is a leaving group, in particular halogen and preferably chloro. The formation of mixed anhydrides of formula (III) and their reaction with compounds of formula (II) is preferably carried out in the temperature range of about −30 to about 10° C., preferably at about −10° C. to about 10° C. more preferably at about −5° C. Preferably the mixed anhydrides of formula (III) are not isolated but are reacted with compounds of formula (II) in a one-pot procedure.

Preferably the formation of the mixed anhydride from compounds (V) and (VI) is carried out in the presence of an organic base such as a tertiary organic amine, for example diisopropylamine, N-methylmorpholine, and trialkylamines such as trimethylamine and triethylamine. Preferred bases include triethylamine. Preferably the compound of formula (V) is mixed with the compound of formula (VI) followed by addition of the amine. This procedure has been found to reduce the need for excess reagents to force the reaction of compounds of formulae (V) and (VI) to completion.

Compounds of formula (V) and (VI) are commercially available or can be prepared using standard procedures. For example the preferred compound of formula (V) where $R^5$, $R^6$ and $R^7$ are methyl and L is chloro is commercially available pivaloyl chloride. The preferred compound of formula (VI) where $R^8$, $R^9$ and $R^{10}$ are methyl is commercially available Boc-glycine.

The mixed anhydride reaction can be carried out in any suitable solvent. Example of suitable solvents include dimethoxyethane, t-butyl methyl ether, THF, chloroform, xylene, toluene and dichloromethane. Preferably the mixed anhydride reaction is carried out using toluene or dichloromethane as solvent, and most preferably dichloromethane.

Preferably the mixed anhydride reaction is carried out under an atmosphere of inert gas, preferably under a nitrogen atmosphere.

Preferably the formation of compounds of formula (IV) is followed by a deprotection step in which the protecting group is removed by any suitable means. Preferably when the protecting group is a Boc group it is removed by acid hydrolysis. This can be carried out in a suitable solvent such as isopropanol. The products of the process are then of such purity that they may be used in pharmaceutical formulations without further purification. Alternatively the product can be purified by conventional means, for example by recrystallisation from a suitable solvent system such as methanol/IPA. In a further aspect the invention therefore provides a process as described above including recrystallisation of the compound of formula (I) or a salt thereof.

Novel intermediates also form an aspect of the invention. Therefore the invention provides a compound of formula (III), as defined above.

Compounds of formula (II) can be prepared by the methods described in European Patent EP 279937. The compound of formula (III) can be prepared by methods well known to those skilled in the art and as illustrated below.

The following conventional abbreviations used in this application will be well known to those skilled in the art:

Cbz benzyloxycarbonyl

Boc tert-butyloxycarbonyl

DCC dicyclohexylcarbodiimide

The invention is illustrated by the following examples.

EXAMPLE 1

Preparation of 2-amino-N-(1,2-diphenyl-1-methylethyl) acetamide hydrochloride (a) 2-(tert-butyloxycarbonylamino)-N-(1,2-diphenyl-1-methylethyl)acetamide A reaction vessel was charged with dichloromethane (360 l) and Boc-glycine (32.6 kg, 186.3 mol). Triethylamine (18.8 kg, 186.1 mol) was added cautiously keeping the temperature below 25° C. The mixture was cooled to below –5° C. and pivaloyl chloride (trimethylacetyl chloride, 22.4 kg, 185.9 mol) in dichloromethane (40 l) was added at such a rate as to keep the temperature below –5° C. This was washed in with dichloromethane (2 l). The mixture was then stirred at below –5° C. for 2–2.5 h and then 1,2-diphenyl-2-propylamine hydrochloride (40 kg, 161.1 mol, dry weight estimate, actual weight including moisture 42.94 kg) was added as a solid through the manway keeping the temperature below –5° C. Triethylamine (28.4 kg, 281.2 mol) was then added keeping the temperature below –5° C. This was washed in with dichloromethane (2 l). The mixture was stirred at below –5° C. for 2.75–3.25 h, water (400 l) was added and the mixture stirred for at least 15 min. The organic layer was separated and washed with dilute hydrochloric acid made up from concentrated hydrochloric acid (40 l) and water (400 l). The organic layer was again separated and then about 80% (360 l) of the dichloromethane was removed by distillation. Isopropyl alcohol (140 l) was then charged and distillation continued until the head temperature reached 80° C. The solution was then cooled and isopropyl alcohol added to make up to a total weight of 200 kg. This solution was then divided in two by weight and each half used directly in the next step.

(b) 2-amino-N-(1,2-diphenyl-1-methylethyl)acetamide hydrochloride

A reaction vessel was charged with half of the product from step (a) in propan-2-ol solution from the above reaction (total weight 100 kg), further propan-2-ol (179.4 kg) and methanol (61.2 l). The vessel was purged with nitrogen and then concentrated hydrochloric acid (15.8 kg) was added to the solution. The solution was heated to reflux for 2–3 h, and then filtered through an in-line filter into a second vessel. The first reaction vessel and the filter were washed through with methanol (8 kg) into the second vessel. The vessel was then heated and the solvent distilled to remove excess methanol. Distillation continued until 125 kg of distillate (a mixture of methanol and propan-2-ol) was removed. The vessel was cooled to –5° C. for about 2 h and the final product filtered off and washed with cold (–5° C.) propan-2-ol (25 l). The product was tray dried under vacuum to give the final product as an off-white solid (21.4 kg, 87% yield overall from 1,2-diphenyl-2-propylamine hydrochloride).

The product was sufficiently pure to be used in pharmaceutical formulations without further purification.

EXAMPLE 2

Preparation of 2-amino-N-(1,2-diphenyl-1-methylethyl) acetamide hydrochloride (Remacemide hydrochloride)

(a) A mixture of 1,2-diphenyl-2-propylamine hydrochloride (40 g, 0.1507 mole) and toluene (100 ml) was stirred at room temperature under a nitrogen atmosphere. Triethylamine (46.1 ml, 0.3315 mole) was added as a single portion and stirring of the resulting mixture was continued.

(b) A mixture of BOC-glycine (30.3 g, 0.1733 mole) and toluene (486 ml) was stirred under a nitrogen atmosphere. Pivaloyl chloride (21.3 ml, 0.1733 mole) was added in a single portion. Immediately after the addition, the contents of the reactor were cooled to –5° C. Triethylamine (17.5 g, 0.1733 mole) was added over one hour with the vessel contents maintained at –5° C. After the addition was complete the resulting mixture was stirred for 2 hours. The 1,2-diphenyl-2-propylamine hydrochloride slurry prepared in (A) was added over 30 minutes with the vessel temperature maintained at –5° C. After this addition was complete, the reaction mixture was stirred for a further 3 hours and then water (250 ml) was added and the internal temperature was allowed to warm to 20° C. The mixture was stirred for 45 minutes and then the toluene layer was then separated off. Analysis, by HPLC, showed 96.4% conversion to the required BOC-remacemide. This solution was used directly in the deprotection step.

(c) A toluene solution of BOC-remacemide (containing an estimated 0.3013 mole of BOC-remacemide) was stirred at 65° C. Hydrochloric acid (52 ml) was added over 10 minutes and then the mixture was stirred at 65° C. for 1.5 hours. A solid precipitated during this time.

The mixture was heated to reflux and solvent collected by distillation. 310 ml of solvent was collected and the distillation head temperature had reached 98° C. The mixture was cooled to −5° C. then filtered and the reaction flask was washed out with toluene (2×30 ml). Damp mass was 127.7 g. The filtered residue was dried in vacuo at 80° C. to give 88.2 g of crude remacemide hydrochloride which represents a yield of 96.1% with respect to 1,2-diphenyl-2-propylamine hydrochloride.

EXAMPLE 3
Crystallisation of Remacemide Hydrochloride

A mixture of remacemide hydrochloride (50 g) and methanol (200 ml) was stirred and warmed to reflux to form a solution. This was the minimum volume of methanol required to form a solution. The solution was filtered through a 0.2 m and then washed through with methanol (12 ml).

The solution was reheated to reflux and solvent was removed by distillation, with 50 ml of distillate being collected. Isopropanol (400 ml) was then added which initiated precipitation. The distillation was continued with another 410 ml of distillate being collected. The mixture was cooled to −5° C., diluted with isopropanol (100 ml) and the purified remacemide hydrochloride was collected by filtration then dried in vacuo at 65° C. The mass of the dried purified material was 46.05 g (92% recovery).

What is claimed is:

1. A process for the production of a compound of formula (I) or a pharmaceutically acceptable salt thereof:

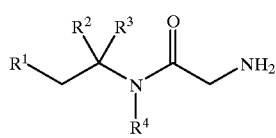

(I)

wherein:
 $R^1$ and $R^2$ are independently phenyl or 4-fluorophenyl;
 $R^3$ is hydrogen, alkyl $C_{1-4}$ or methoxycarbonyl;
 $R^4$ is hydrogen or methyl;
which comprises reaction of a compound of formula II:

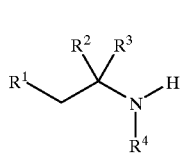

(II)

in which $R^1$, $R^2$, $R^3$ and $R^4$ are as defined in formula (I), with a compound of formula (III):

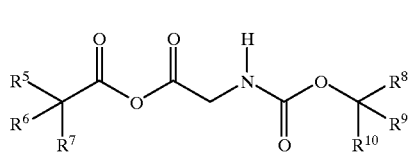

(III)

in which $R^5$, $R^6$, $R^7$, $R^8$, $R^9$ and $R^{10}$ are independently $C_{1-6}$ alkyl to give a compound of formula (IV):

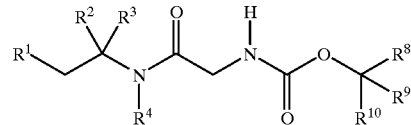

in which $R^1$, $R^2$, $R^3$, $R^4$, $R^8$, $R^9$ and $R^{10}$ are as defined in formula (I), followed by deprotection and optionally thereafter forming a pharmaceutically acceptable salt.

2. A process as claimed in claim 1 in which $R^1$ and $R^2$ are both phenyl.

3. A process as claimed in claim 1 in which $R^3$ is $C_{1-4}$alkyl.

4. A process as claimed in claim 1 in which $R^4$ is hydrogen.

5. A process according to claim 1 in which $R^1$, $R^2$, $R^3$, $R^8$, $R^9$ and $R^{10}$ are all methyl.

6. A process according to claim 1 in which the compound of formula I is 2-amino-N-(1,2-diphenyl-1-methylethyl)acetamide, or a pharmaceutically acceptable salt thereof.

7. A process according to claim 1 in which the mixed anhydride reaction is carried out in the temperature range of about −30 to about 10° C.

8. A process according to claim 1 in which the mixed anhydride reaction is carried out at about −5° C.

9. A process according to claim 1 in which the mixed anhydride reaction is carried out using dichloromethane as solvent.

10. A process according to claim 1 in which the mixed anhydride reaction is carried out under a nitrogen atmosphere.

11. A process according to claim 1 in which the compound of formula (III) is prepared by mixing a compound of formula (V):

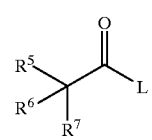

(V)

in which $R^5$, $R^6$ and $R^7$ are as defined in formula (III) and L is a leaving group with a compound of formula (VI):

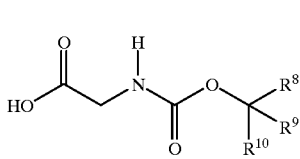

(VI)

in which $R^8$, $R^9$ and $R^{10}$ are as defined in formula (III) followed by addition of an organic amine.

12. A process according to claim 11 in which the organic amine is triethylamine.

13. A process according to claim 1 in which the mixed anhydride reaction is followed removal of the protecting group from the compound of formula (IV) by acid hydrolysis.

14. A process according to claim 1 which further comprises recrystallisation of the compound of formula (I) or a salt thereof.

15. A process according to claim 14 in which the recrystallisation is carried out using methanol/IPA.

16. A process according to claim 14 in which the compound of formula (I) is 2-amino-N-(1,2-diphenyl-1-methylethyl)acetamide hydrochloride.

* * * * *